United States Patent [19]

Boucher, Jr. et al.

[11] Patent Number: 5,725,842
[45] Date of Patent: *Mar. 10, 1998

[54] METHOD OF ADMINISTERING AMILORIDE

[75] Inventors: Richard C. Boucher, Jr.; Michael R. Knowles, both of Chapel Hill, N.C.

[73] Assignee: The University of North Carolina at Chapel Hill, Chapel Hill, N.C.

[*] Notice: The term of this patent shall not extend beyond the expiration date of Pat. No. 5,292,498.

[21] Appl. No.: 583,671

[22] Filed: Jan. 5, 1996

Related U.S. Application Data

[63] Continuation of Ser. No. 218,839, Mar. 28, 1994, abandoned, which is a continuation of Ser. No. 908,579, Jun. 29, 1992, abandoned, which is a continuation of Ser. No. 593,193, Oct. 5, 1990, abandoned.

[51] Int. Cl.$^6$ ............................................. A61K 9/12
[52] U.S. Cl. ........................... 424/45; 424/46; 514/255; 514/851
[58] Field of Search ........................ 424/45, 46; 514/255, 514/851

[56] References Cited

U.S. PATENT DOCUMENTS

| | | | |
|---|---|---|---|
| 3,313,813 | 4/1967 | Cragoe, Jr. ............................. | 260/250 |
| 4,501,729 | 2/1985 | Boucher et al. ......................... | 424/45 |
| 5,100,647 | 3/1992 | Agus et al. ............................. | 424/45 |
| 5,162,348 | 11/1992 | Glass .................................... | 514/359 |
| 5,292,498 | 3/1994 | Boucher, Jr. ........................... | 424/45 |

OTHER PUBLICATIONS

I.M. Bowler, Nebulised amiloride in respiratory exacerbations of cystic fibrosis: a randomised controlled trial, *Archives of Disease in Childhood* 73, 427–30 (1995).

M. Knowles et al., *New Eng. J. Med.* 322, No. 17, 1189–1194 (1990).

*Primary Examiner*—Raj Bawa
*Attorney, Agent, or Firm*—Bell, Seltzer, Park and Gibson, P.A.

[57] ABSTRACT

Methods are disclosed for removing retained mucus secretions from the lungs of a human subject. The method includes (1) generating an aerosol suspension of respirable solid, dry particulate amiloride, and (2) delivering by inhalation the aerosol suspension to the respiratory system of the subject. The solid particulate amiloride is comprised of particles of about 1 to 5 microns and is free of liquid amiloride particles. The aerosol suspension of respirable solid particulate amiloride is administered in an amount sufficient to achieve concentrations of amiloride on the airway surfaces of from about $10^{-7}$ to $10^{-3}$ Moles/liter. As a result of the treatment, the secretions are hydrated and more easily transported from the lung via mucociliary action. Methods are also disclosed for the treatment of cystic fibrosis in humans.

16 Claims, 7 Drawing Sheets

METHOD OF ADMINISTERING AMILORIDE

This is a continuation of application Ser. No. 08/218,839 filed Mar. 28, 1994, which is a File Wrapper Continuation of application Ser. No. 07/908,579 filed Jun. 29, 1992, which is a File Wrapper Continuation of application Ser. No. 07/593,193 filed Oct. 5, 1990 all abandoned.

This invention was made with Government support under Grant No. HL34322, awarded by the National Institutes of Health. The Government has certain rights in the invention.

FIELD OF THE INVENTION

This invention relates to a method of removing retained mucus secretions from the lungs of a patient by administering the patient an aerosol suspension of respirable solid particulate amiloride.

BACKGROUND OF THE INVENTION

Cystic fibrosis (CF) is among the most prevalent, lethal diseases of genetic origin. In this disease, abnormal ion transport across the respiratory epithelia leads to dehydrated, viscous and poorly-cleared airway secretions that contribute to chronic infection of the airways and early death. Knowles, 11 Clin. Chest. Med. 75 (1986). The action of amiloride, a diuretic, to inhibit $Na^+$ and water absorption when applied to the luminal membrane of airway epithelia, led to the hypothesis that amiloride might inhibit excessive $Na^+$ absorption in CF patients and thereby "liquify" airway secretions to provide a beneficial effect on mucociliary clearance and long-term pulmonary function. See, e.g., Knowles, 221 Science 1067 (1983), Waltner, 8 Trends in Pharm. Sci. 316-320 (1987). Because an effective concentration of amiloride cannot be achieved in the airway lumen by oral administration, this drug must be administered as an aerosol to achieve its therapeutic potential. The administration of amiloride as an aerosol is described in U.S. Pat. No. 4,501,729 to Boucher et al.

A pilot study has confirmed clinical benefit of amiloride aerosol when administered as a liquid aerosol. See Knowles, 332 N. Engl. J. Med. 1189 (1990). However, while the administration of a liquid aerosol provides a useful means of treatment, it also has several limitations. It is time-consuming for the patient, not easily portable, and the dosage is limited by the low solubility of amiloride in the nebulizer solution. Consequently, an object of the present invention is to further improve and refine methods for the administration of amiloride aerosols.

SUMMARY OF THE INVENTION

A method of removing retained mucus secretions from the lungs of a subject in need of such treatment is disclosed. The method comprises delivering by inhalation an aerosol suspension of respirable solid particulate amiloride to the respiratory system of said subject in an amount sufficient to achieve effective concentrations of amiloride on the airway surfaces of said subject (e.g., from about $10^{-7}$ to about $10^{-3}$ Moles/liter). As a result of the treatment, the secretions are hydrated and more easily transported from the lung via mucociliary action.

A second aspect of the present invention is a pharmaceutical composition comprised of solid particulate amiloride, the composition comprising particles of respirable size (e.g., about 1 to 5 microns). The composition may be provided as a prepackaged unit containing a dose of from about 1 to 20 milligrams of respirable size particles.

A third aspect of the present invention is the use of respirable solid particulate amiloride for the manufacture of a medicament for removing retained mucus secretions from the lungs of a subject in need of such treatment.

Also disclosed is an apparatus for administering an aerosol of a solid particulate medicament (e.g., Amiloride) to the lungs of a patient. The apparatus comprises a solid particulate medicament aerosol generator and an impactor assembly for removing large particles of medicament from the aerosol produced by the aerosol generator. The impactor assembly comprises an enclosed chamber having an inlet opening and an outlet opening formed on opposite sides thereof, with the inlet opening having an area of from about 50 to about 150 square millimeters. The aerosol generator is connected to the inlet opening. A first impactor plate is positioned in the chamber, with the first impactor plate adjacent the inlet opening. The first impactor plate has an uninterrupted primary impaction surface formed thereon, with the primary impaction surface substantially axially aligned with the inlet opening and having a diameter not less than the inlet opening. The primary impaction surface is spaced away from the inlet opening a distance of from about 5 to about 15 millimeters. The first impactor plate has at least one exhaust opening formed therein in fluid communication with the outlet opening.

In preferred embodiment of the foregoing apparatus, the at least one exhaust opening formed in the first impactor plate comprises at least one jet opening having a total area of from about 50 to about 150 square millimeters. The preferred apparatus further comprises a second impactor plate positioned in the chamber in spaced relation to the first impactor plate. The second impactor plate is downstream from the first plate with respect to the direction of aerosol flow in the impactor assembly. The second impactor plate has an uninterrupted secondary impaction surface formed thereon substantially parallel to each of the at least one jet openings formed in the primary impactor plate, with each of the secondary impaction surfaces axially aligned with each of the jet openings and having a width not less than each of said jet openings. Each of the secondary impaction surfaces is spaced apart from the corresponding jet opening a distance of from about 5 to 15 millimeters. The second impactor plate has at least one exhaust opening formed therein in fluid communication with the outlet opening of the enclosed chamber.

DETAILED DESCRIPTION OF THE PREFERRED EMBODIMENTS

Figure 1:
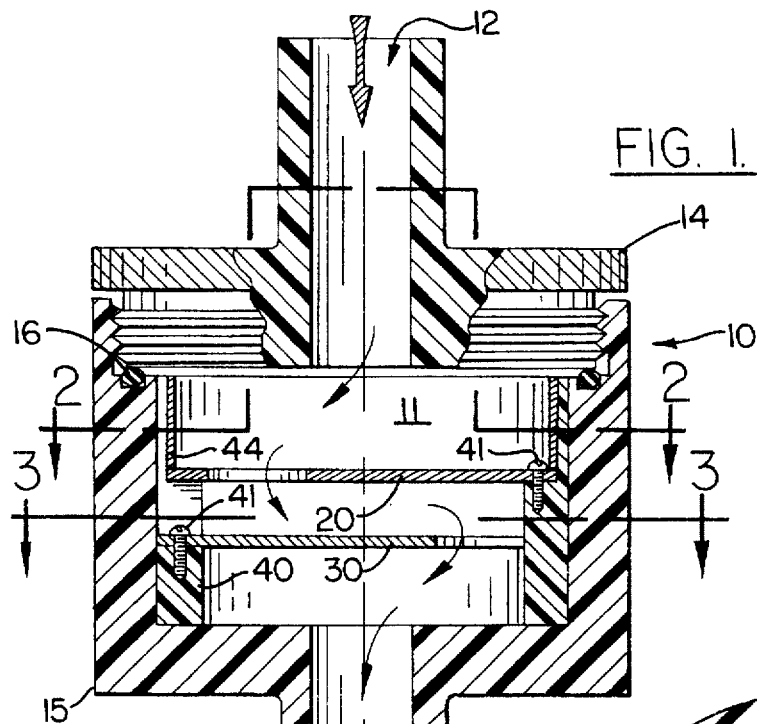
FIG. 1 is a side-sectional view of an impactor assembly of the present invention.
Figure 2:
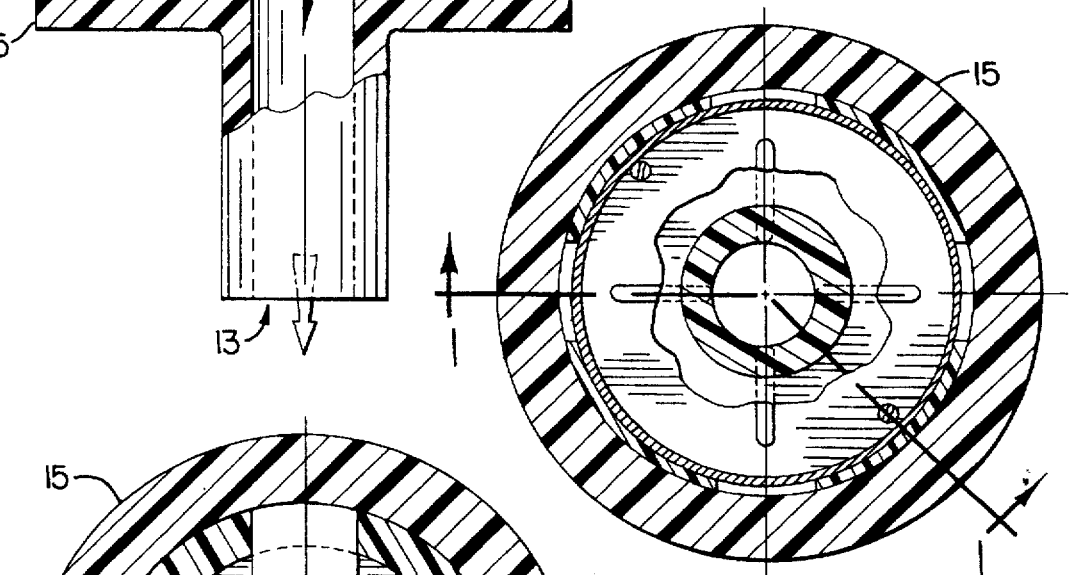
FIG. 2 is a cross-sectional view of the impactor assembly, taken along the line 2—2 of FIG. 1, illustrating the relationship between the inlet port and the first impactor surface jets.
Figure 3:
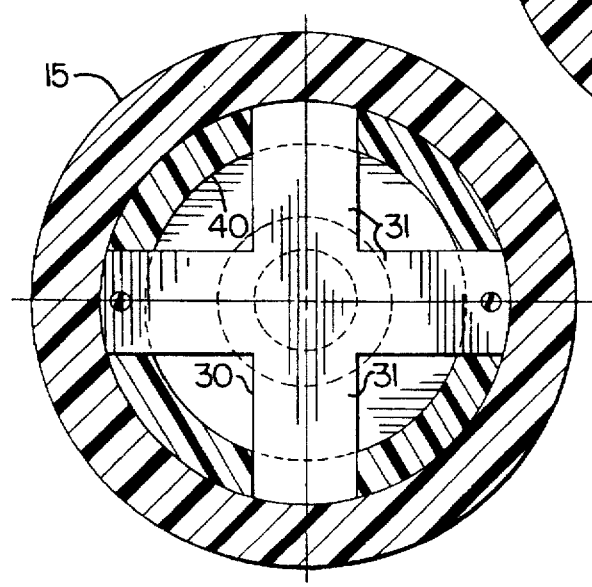
FIG. 3 is a cross-sectional view of the impactor assembly, taken along the line 3—3 of FIG. 1, illustrating the placement of the second impactor surface.

The method of the present invention may be used to remove mucus secretions retained in the lungs of a subject for any reason, including (but not limited to) retention of secretions arising from airway diseases such as cystic fibrosis, chronic bronchitis, asthma, and bronchiectasis.

Amiloride is disclosed in U.S. Pat. No. 3,313,813 to E. Cragoe. The administration of amiloride to the lungs is disclosed in U.S. Pat. No. 4,501,729 to R. Boucher, J. Gatzy, and M. Knowles. The disclosures of these and all other patent references cited herein are to be incorporated herein by reference. Amiloride compositions may be prepared by the procedures disclosed in U.S. Pat. No. 3,313,813, in combination with procedures known to those skilled in the art. Compositions containing respirable dry particles of micronized amiloride may be prepared by grinding dry amiloride with a mortar and pestle, and then passing the micronized composition through a 400 mesh screen to break up or separate out large agglomerates.

Solid particulate amiloride prepared for practicing the present invention should include particles of respirable size: that is, particles of a size sufficiently small to pass through the mouth and larynx upon inhalation and into the bronchi and alveoli of the lungs. In general, amiloride particles ranging from about 1 to 5 microns in size (more particularly, less than about 4.7 microns in size) are respirable.

Amiloride used to prepare solid particulate amiloride compositions for the present invention may be in the form of a pharmaceutically acceptable salt (i.e., amiloride hydrochloride) or a free base of amiloride. Because the free base is less soluble than the salt, free base compositions are employed to provide more sustained release of amiloride to the lungs. Amiloride present in the lungs in particulate form which has not gone into solution is not available to induce a physiological response, but serves as a depot of bioavailable drug which gradually goes into solution.

The solid particulate amiloride composition may optionally contain a dispersant which serves to facilitate the formation of an aerosol. A suitable dispersant is lactose, which may be blended with the amiloride in any suitable ratio (e.g., a 1 to 1 ratio by weight).

In one embodiment of the invention, the solid particulate amiloride composition may contain both a free base of amiloride and a pharmaceutically acceptable salt such as amiloride hydrochloride to provide both early release of and sustained release of amiloride for dissolution into the mucus secretions of the lungs. Such a composition serves to provide both early relief to the patient, and sustained relief over time. Sustained relief, by decreasing the number of daily administrations required, is expected to increase patient compliance with a course of amiloride treatments.

The dosage of amiloride administered may be the same as that disclosed in U.S. Pat. No. 4,501,729: i.e., an amount sufficient to achieve dissolved concentrations of amiloride on the airway surfaces of the subject of from $10^{-6}$ to $10^{-4}$ Moles/liter. Depending upon the condition being treated the dose may be somewhat lower or higher, ranging from an amount sufficient to achieve concentrations of dissolved amiloride on the airway surfaces of the subject of about $10^{-7}$ to about $10^{-3}$ Moles/liter. The daily dose by weight may range from about 1 to 20 milligrams of respirable amiloride particles for a human subject, depending upon the age and condition of the subject. Depending upon the solubility of the particular amiloride formulation administered, the daily dose may be divided among one or several unit dose administrations. A currently preferred unit dose is about 2 milligrams of respirable amiloride particles given at a regimen of four administrations per day. The dosage may be provided as a prepackaged unit by any suitable means (e.g., encapsulating in a gelatin capsule).

Any solid particulate medicament aerosol generator may be used to practice the present invention, with specific examples being given below. Aerosol generators for administering solid particulate medicaments to a human subject produce particles which are respirable, as explained above, and generate a volume of aerosol containing a predetermined metered dose of a medicament such as solid particulate amiloride at a rate suitable for human administration. One illustrative type of aerosol generator comprises a chamber having a rotor mounted therein, which rotor carries a gelatin capsule containing a metered dose of dry particle medicament. In use the capsule is pierced, a patient inhales through the chamber, and the rotor is caused to spin at a speed sufficient to dispense the medicament to thereby form an aerosol of dry particles. A second type of illustrative aerosol generator comprises a pressurized canister containing dry particle medicament in a propellant. The propellant is discharged through a metering valve configured to dispense a metered dose of the dry particle medicament into the atmosphere. The propellant evaporates, leaving an aerosol of dry particle medicament.

The aerosol may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

An impactor assembly useful for administering solid particulate amiloride is illustrated in FIGS. 1 through 4. This assembly is particularly well suited for the administration of aerosols of solid particulate medicaments to the lungs of human patients at a flow rate of about 60 liters/minute. Note that, depending on the aerosol generator employed, flow rate may be wholly or partially dependent on the rate of breathing of the subject. Thus, while this apparatus has been optimized for a flow rate particularly suitable for administration of an aerosol by inspiration of a human subject, those skilled in the art will appreciate that adjustments can be made to the illustrated apparatus to accomodate different flow rates.

The impactor assembly 10 of FIGS. 1 through 4 comprises an enclosed chamber 11 having an inlet opening 12 and a outlet opening 13 formed on opposite sides thereof. While the shape of these openings as illustrated is round, the shape is not critcal. The chamber, which is cylindrical in shape, is formed of a cap unit 14 threaded into a body unit 15. An O-ring 16 is provided to seal the union between the units. While the volume of the chamber is not critical, it suitably has a diameter of from about 25 to 60 millimeters. The inlet opening has an area, in cross section, of about 100 square millimeters, but this area can be varied from about 50 to about 150 square millimeters to accomodate different rates of flow. The cross sectional area of the outlet opening may be the same as or larger than that of the inlet opening, but no smaller than that of the inlet opening.

Figure 4:
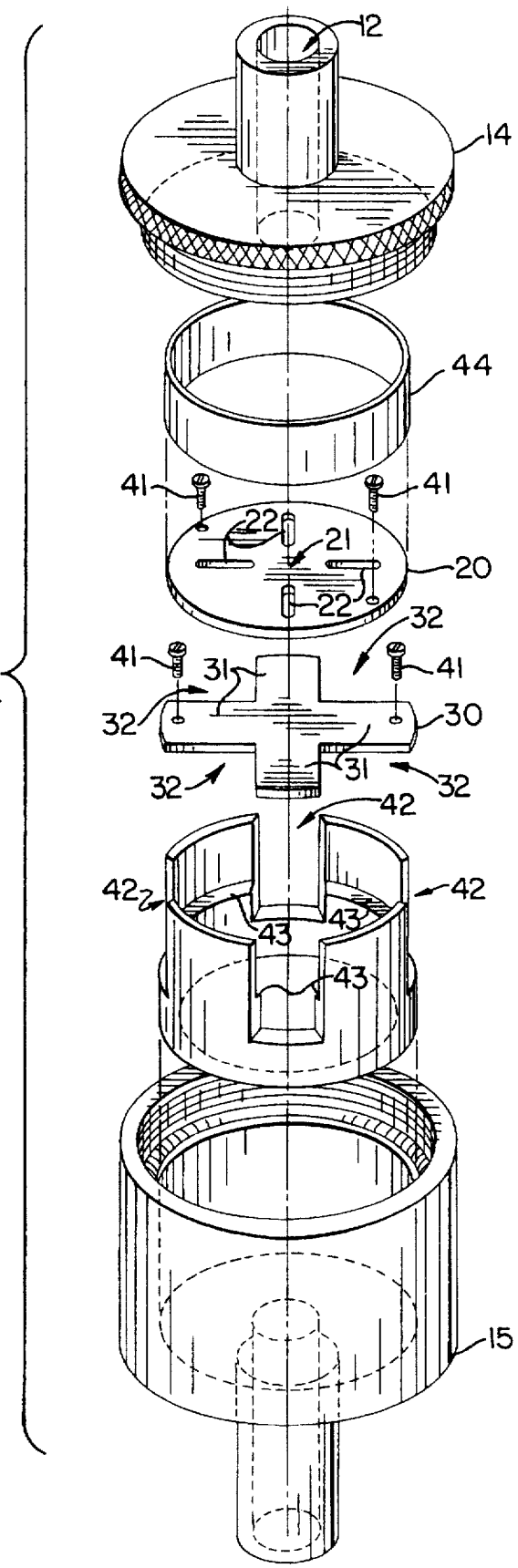
FIG. 4 is an isometric exploded view of the impactor assembly of FIGS. 1-3.

First and second impactor plates 20, 30 are positioned in the enclosed chamber in spaced relation to one another. The first impactor plate 20 is positioned adjacent the inlet opening 12, and the second impactor plate is positioned downstream from the first impactor plate with respect to the direction of flow (indicated by arrows in FIG. 1). The impactor plates are carried by a hollow, cylindrically shaped insert 40 which has an outer diameter substantially the same as the inner diameter of the enclosed chamber so that the insert fits snugly into the chamber. The plates are fastened the the insert with screws 41. As best shown in FIG. 4, grooves 42 are formed in the insert to carry the second impactor plate 30, and a shoulder 43 is formed on the interior of the insert to provide the proper spaced relation between the first and second impactor plates 20, 30. A steel band 44 is provided within the insert 40 above the first impactor plate to prevent the short-circuit of aerosol flow around the first impactor plate through the grooves formed in the insert. In the illustrated embodiment the enclosed chamber and insert are suitably made from Plexiglas™ and the primary and secondary impactor plates made from brass, but a broad variety of suitable materials and fabrication techniques are available. For example, the entire impactor assembly could be formed of a molded plastic material.

An uninterrupted primary impaction surface 21 is formed on the first impactor plate. The primary impaction surface is substantially axially aligned with the inlet opening and has a diameter not less than the inlet opening so that larger particles in an aerosol stream passing through the inlet opening will be carried by inertia into the primary impaction surface. The impaction surface may be coated with amy suitable sticking agent, such as silicone stopcock grease, so that particles which strike the surface adhere thereto.

The distance of the primary impaction surface from the inlet opening will effect the size of the particles which are carried by inertia into the primary impaction surface. In the illustrated embodiment this distance is 7 millimeters from the point at which the inlet opening enters the enclosed chamber, but may suitably be from about 2 to 15 millimeters.

The first impactor plate 20 has a plurality of elongate slots 21 formed therein which serve as jet openings. The slots should have a width of from about 1 to 3 millimeters, and most preferably about 2 millimeters. As illustrated, the first impactor plate has four rectangular slots formed therein, with each slot being 13 millimeters long by 1.9 millimeters wide. Other suitable alternatives are to provide a single spiral-shaped slot or a set of interconnected slots (e.g., arranged in a "Z" shape), to provide slots of varying widths, etc. Preferably, the long sides of the slots are substantially parallel to one another so that velocity through the slots is uniform. The total cross sectional area of the jet openings may be from about 50 to about 150 square millimeters, or more preferably from about 80 to 120 square millimeters, but is most preferably about 100 square millimeters.

The second impactor plate 30 has an uninterrupted secondary impaction surface 31 formed thereon substantially parallel to each of the jet openings formed in the first impactor plate. As illustrated, the secondary impaction surfaces are the four arms of the second impactor plate. Each of the secondary impaction surfaces is axially aligned with each of the corresponding jet openings, and has a width not less than each of the jet openings, so that larger particles in an aerosol stream passing through the jet openings will be carried by inertia into the secondary impaction surfaces. The secondary impaction surfaces may be coated with a sticking agent in the same manner as the primary impaction surface.

As with the primary impaction surface, the distance of the secondary impaction surfaces from the corresponding jet openings wills effect the size of the particles which are carried by inertia into the secondary impaction surfaces. In the illustrated embodiment this distance is 7 millimeters, but again may suitably be varied from about 2 to 15 millimeters. This dimension should, however, be greater than the width of the jet openings.

The second impactor plate 30 has a plurality of exhaust openings 32 formed therein which are in fluid communication with the chamber outlet opening. In an alternative embodiment of the invention, the back wall of the chamber could serve as the second impactor plate and the exhaust opening of the second impactor plate could be the outlet opening: this would simply involve dimensioning the chamber to provide the appropriate spacing between the jet openings formed in the primary impactor plate and the back wall of the enclosed chamber.

The present invention is explained in greater detail in the Examples which follow. These examples are intended as illustrative of the invention, and are not to be taken as limiting thereof.

EXAMPLE 1

Solubility of Respirable Solid Amiloride Particles in Plasma

This example shows that solid particles of amiloride hydrochloride which are sufficiently small to be respirable (˜1 μm) provide a timed release effect (i.e., are dissolved slowly over time) in an aqueous solution which approximates the ionic strength of plasma.

Freshly excised human cystic fibrosis airway epithilia is used to assay bioactive amiloride in solution. Freshly excised tissues is obtained from the Operating Room at The University of North Carolina Hospitals as previously described. R. Boucher, M. Stutts, M. Knowles, L. Cantley, and J. Gatzy, Na+ transport in cystic fibrosis respiratory epithelia. Abnormal basal rate and response to adenylate cyclase activation. *J. Clin. Invest.* 78, 1245–1252 (1986). The tissue preparation is mounted in a minature Ussing chamber that has 6 ml of solution bathing each (mucosal; basolateral) surface of the preparation. The solution is a Krebs-Ringer bicarbonate solution which approximates the ionic composition of plasma. This solution is warmed (37°) and circulated with a gas lift (95% oxygen, 5% $CO_2$) system. Mixing time in this chamber has been previously measured by calibration with dyes (blue dextran) and is five seconds or less. The measurement of sodium transport rates is performed using a voltage clamp that is interfaced to the tissue preparation by pairs of potential sensing electrodes and current passing electrodes. The current required to null the transepithelial potential difference to zero is the short circuit current, which in human airway tissue is an accurate index of sodium transport rates. See R. Boucher et al., supra.

Figure 5:
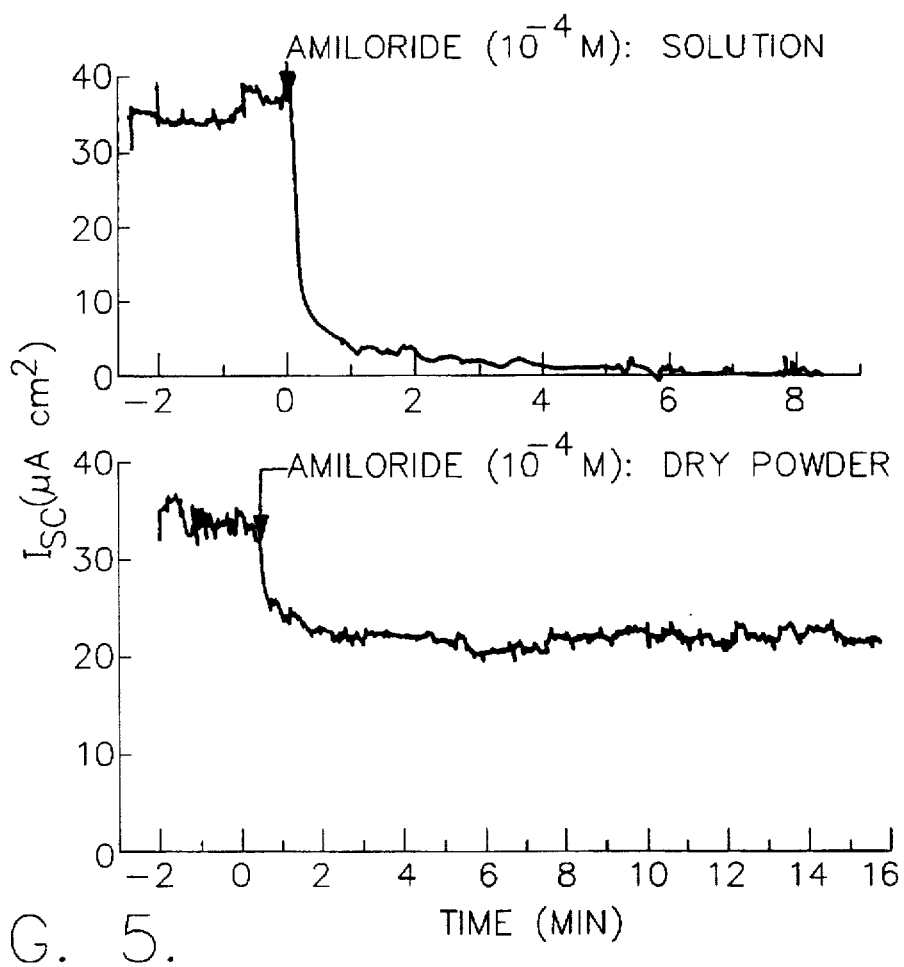
FIG. 5 shows a comparison of the effects of Amiloride formulation solution (top) vs. dry powder (bottom) on the kinetics of Inhibition of $Na^+$ transport rates by cystic fibrosis airway epithelia.

FIG. 5 shows a comparison of the effects of Amiloride Hydrochloride Formulation [solution (top) vs. dry powder (bottom)] on the kinetics of inhibition of $NA^+$ transport rates by Cystic Fibrosis airway epithelia. This experiment was conducted as described above. Complete Inhibition of $I_{SC}$ was achieved at about sixty minutes. Particle size of the dry powder was about 1 μm.

EXAMPLE 2

Apparatus for Administering Solid Particulate Amiloride to the Lungs

The present invention was tested using two devices that generate dry particle aerosols, the Spinhaler™ from Fisons, Inc., See Bell, *J. Pharm. Sci.* 60, 1559 (1971); Cox, *Brit. Med. J.* 2, 634 (1969), and the metered-dose inhaler (MDI). The Spinhaler™ consists of a rotor that holds a gelatin capsule containing the dry amiloride powder. After the capsule is pierced, the patient inhales through the mouthpiece causing the rotor to spin and vibrate at a high speed, dispensing and dispersing the drug. The MDI consists of a pressurized canister containing the drug, the propellant, and a surfactant. When activated, the MDI spray disperses the drug within large droplets of propellant into a spacer. Evaporation of the propellant and sedimentation of the larger particles yield dry drug that is inhaled by the patient.

The total dose a patient receives (systemic dose) is the sum of the dose to the pulmonary conducting airways (respirable dose) plus the dose associated with drug collection in the mouth and throat (oropharyngeal dose). A pharmacokinetic study using liquid amiloride aerosolized from a nebulizer indicates that the optimal respirable dose of dry powder amiloride generated is 8 to 12 mg daily whereas the maximum systemic dose is 20 mg daily. This result was based on the dose necessary to achieve an effective concentration of amiloride in the airway surface liquid. Thus, apparatus was developed to generate the necessary respirable dose without exceeding the maximum systemic dose. To reach this objective, the generation rate and size distribution of the aerosolized drug had to be controlled.

Particles are considered respirable if they are smaller than about 4.7 μm in aerodynamic diameter. The true respirable mass depends jointly on the the size distribution of the aerosol particles as well as the collection characteristics of the lung airways. The collection characteristics of the lung airways vary with age and are affected by disease. Thus, true respirable mass will vary from patient to patient and cannot be determined accurately.

Without a spacer or an impactor, the size distributions of amiloride particles generated using an MDI or the Spinhaler™ are coarse. As a result, oropharyngeal deposition is high. When a spacer or impactor is used, most of the particles larger than about 5 μm are removed from the aerosol with the result that oropharyngeal deposition decreases substantially.

Using the MDI with spacer and impactor, or using the Spinhaler™ with the impactor, the target of 12 mg/day of respirable amiloride can be generated without exceeding a systemic dose of 20 mg/day. The MDI with spacer and impactor requires about 50 puffs/day to generate the 12 mg dose, whereas the Spinhaler™ with impactor requires inhaling the contents of about five capsules to generate the 12 mg respirable dose. If the therapeutic dose of amiloride is reduced to 8 mg/day, then the MDI with the spacer alone is capable of generating this amount using 17 puffs/day without exceeding the maximum allowable systemic dose.

Figure 6:
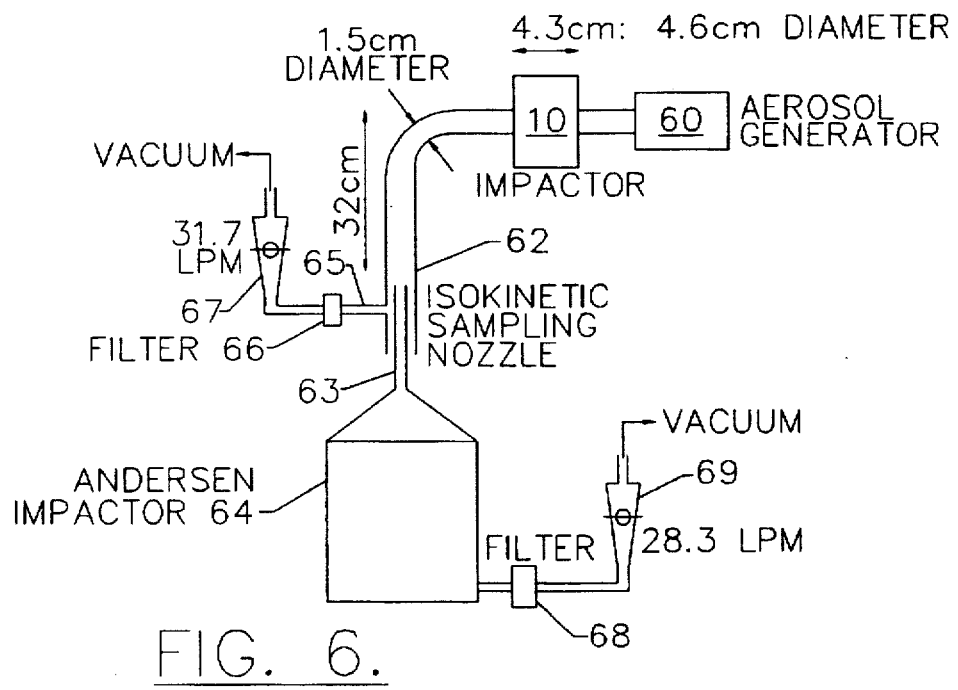
FIG. 6 illustrates apparatus used to test the impactor shown in FIGS. 1 through 4.

FIG. 6 is a drawing of the experimental apparatus used in these studies. For the Spinhaler™ tests, lactose was used as a flow aid to dispense amiloride from the capsules. Before use, the lactose was not micronized, but was shaken through a 400 mesh sieve so that all lactose particles used were smaller than 37 um. Amiloride was then mixed with the lactose in a 1:1 ratio and the material was reshaken through the 400 mesh sieve to break apart any agglomerates. Then 58 mg of the resieved mixture of amiloride and lactose was placed in a capsule with pre-drilled holes and loaded into the Spinhaler™. Air at 60 liters per minute (Lpm) flowed in succession through the aerosol generator 60 (a Spinhaler™), an impactor 10 as described in connection with FIGS. 1–4 above, a glass "throat" 61, and a plastic "distal pharynx" 62. Within the distal pharynx an isokinetic sample at 28.3 Lpm flowed through a nozzle 63 and into an Andersen impactor 64. The remaining 31.7 Lpm of the original 60 Lpm was drawn off through a bypass line 65 that led to a filter 66, a rotameter 67, and to a vacuum (not illustrated). Gas that left the Andersen impactor flowed through a filter 68 to a second rotameter 69 to vacuum. To conduct a test, vacuum was applied simultaneously to both the Andersen impactor and the bypass lines. Air flow at 60 Lpm was maintained for four seconds to simulate an inspiration; six inspirations were used for each capsule of drug tested.

Amiloride used with the MDI was first milled until essentially all particles were smaller than 2.6 μm in diameter as determined using an optical microscope. This amiloride was then packaged in an MDI with Freon propellants (trichlorofluoromethane and dichlorodifluoromethane) and a surfactant (sorbitan trioleate), added to break up droplets or aggregates of solid particles. A Nebuhaler™ spacer 27 cm long, (see Newman, 39 Thorax 935 (1984)), was attached to the MDI to allow evaporation of the propellant and to remove larger particles by sedimentation. Prior to each release of drug from the MDI, the canister was shaken vigorously to achieve homogeneity. In each test, the MDI aerosol was dispersed into the spacer via a 50 μl metering valve designed to deliver 1 mg amiloride per puff; however, the actual delivery was closer to 3 mg/puff as determined by spectrophotometric analysis of all amiloride collected as discussed below. Leakage of some liquid from the MDI canisters between the filling time and the actual usage would have increased the concentration of amiloride without affecting internal canister pressure. Following the dispersion and a one second delay, vacuum was applied to both the Andersen impactor and bypass lines and maintained for four seconds. This procedure was repeated for a total of six aerosol puffs from the MDI for each test. The MDI tests, like the Spinhaler™ tests, used a total flow of 60 Lpm; 28.3 to the Andersen impactor and 31.7 Lpm through the bypass line.

Tests were conducted with the MDI and spacer both with and without the impactor. The fractional efficiency of the impactor was determined by comparing the mass of amiloride collected on each stage of the Andersen impactor with and without the impactor in place.

Each plate of the Andersen impactor was coated with silicone stopcock grease dissolved in hexane. Hinds, *Aerosol Technology*, John Wiley & Sons, New York, 1982. The impactor, when used, was coated with sprayed-on silicone grease. After each experiment, the apparatus was disassembled and each component washed individually with 50 ml of distilled water to remove amiloride and lactose particles. The impactor, when used, was washed with 100 ml of methanol. The components analyzed for amiloride included the Spinhaler™ and its used capsule, the Nebuhaler™ spacer when used, the impactor when used, the glass throat, the distal pharynx, and the sidearm filter, plus the entry nozzle, six individual plates, and final filter of the Andersen impactor. Washes from each of these components were then analyzed for amiloride. Two calibration curves were generated using pre-weighed masses of amiloride dissolved in distilled water or methanol. The standards and samples were assayed at 361 nm on a Beckman DU-40 Series Spectrophotometer. Lactose did not interfere with amiloride absorbance at 361 nm. These data were used to determine the concentration of amiloride in each wash sample.

With these data we could calculate the mass of amiloride in each test that was left in the capsule and Spinhaler™ (or MDI and spacer), the amount caught in the impactor when used, the "oropharyngeal" dose (mass caught in throat, distal pharynx, and Andersen impactor stages for particles larger than 4.7 um), and the "respirable" dose (mass in Andersen impactor stages for particles smaller than 4.7 um). Actual masses collected in the Andersen impactor, which operated at 28.3 Lpm, were adjusted to account for the total air flow through the system, 60 Lpm, by multiplying the Andersen catches by the ratio of 60/28.3.

Figure 7:
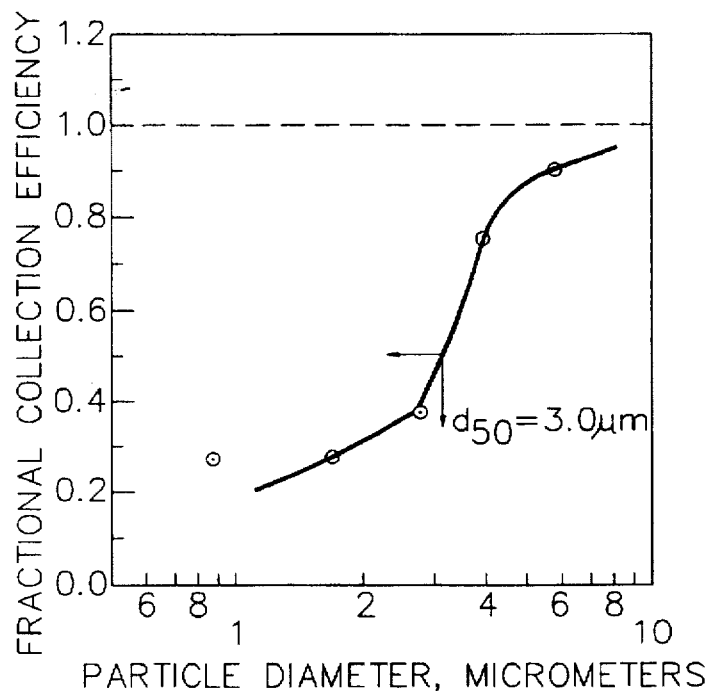
FIG. 7 is a graph of the collection efficiency v. aerodynamic particle diameter for the experimental impactor.
Figure 8:
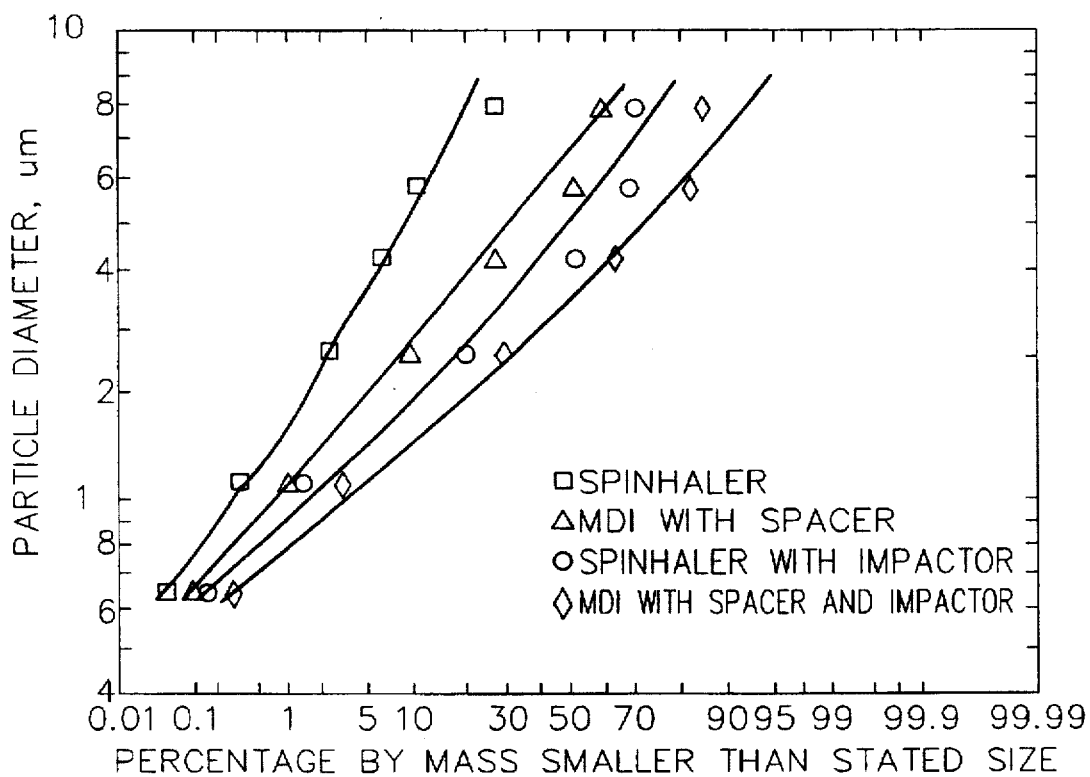
FIG. 8 is a graph of the cumulative size distributions for amiloride aerosols generated by the Spinhaler™ alone, the metered-dose inhaler (MDI) with spacer alone, by the Spinhaler™ with the impactor, and by the MDI with spacer and impactor.

The fractional efficiency curve for the impactor is shown in FIG. 7. The impactor collected almost all particles larger than about 6 micrometers in aerodynamic diameter, and passed most particles smaller than about 2 micrometers in aerodynamic diameter.

The size distributions for the amiloride delivered by the Spinhaler™ alone, the Spinhaler™ with the impactor, the MDI with the spacer alone, and the MDI with spacer and impactor are shown in FIG. 7. This figure shows that the Spinhaler™ alone produces a coarse aerosol with mass median diameter (mmd) substantially larger than 10 um. The MDI with spacer yields a somewhat finer aerosol, with mmd of about 6 um. The size distributions of the aerosols after passing through the impactor were smallest, with mmd values of about 4 and about 3 um after generation in the Spinhaler™ and in the MDI with spacer, respectively, in keeping with expectations based on the fractional efficiency curve for the impactor.

Figure 9:
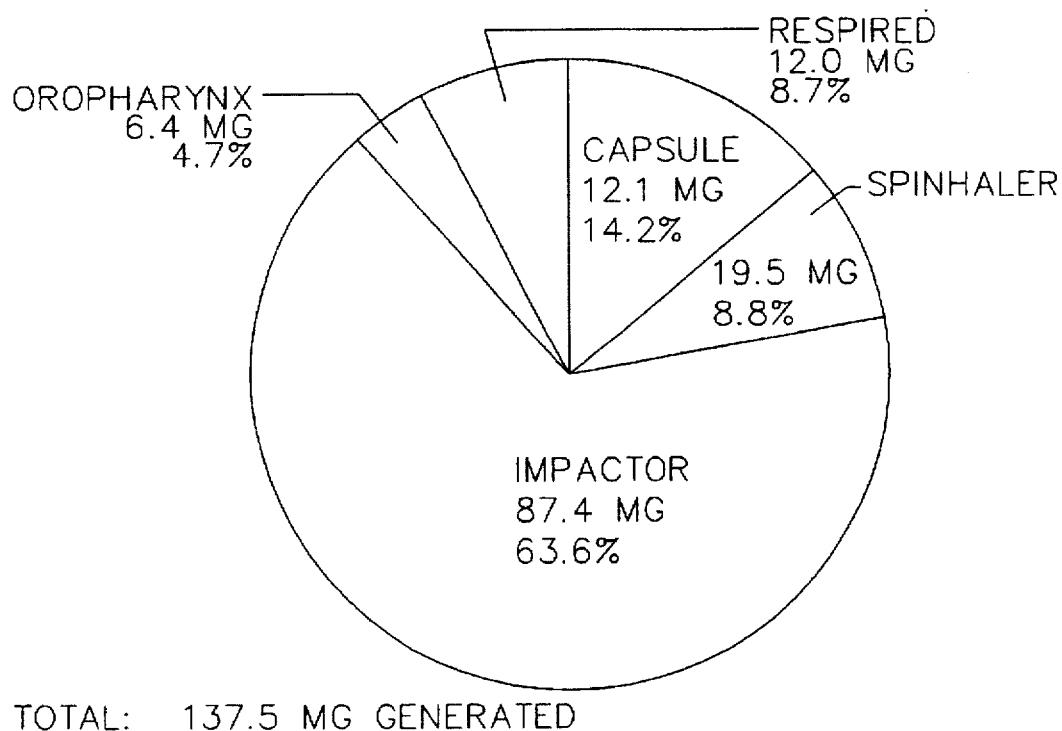
FIG. 9 is a chart of the fate of amiloride generated by the Spinhaler™ and impactor when 12 mg of respirable amiloride are produced.
Figure 10:
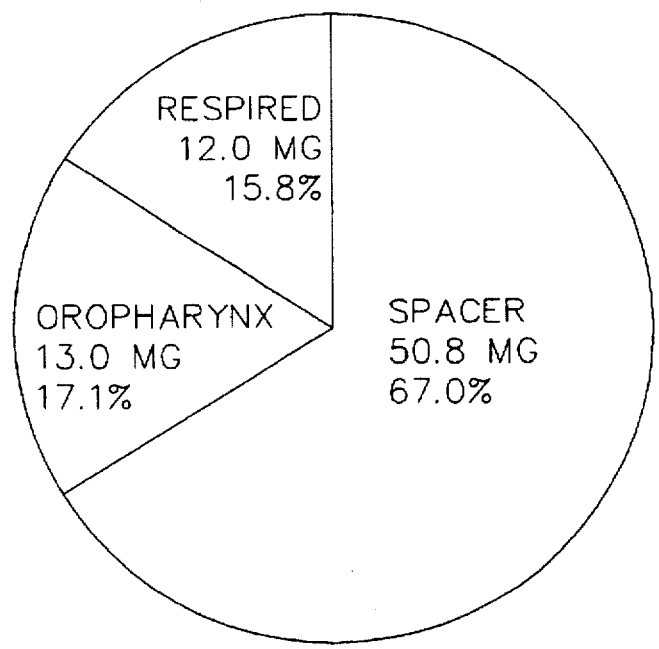
FIG. 10 is a chart of the fate of amiloride generated by the MDI with spacer alone when 12 mg of respirable amiloride are produced.
Figure 11:
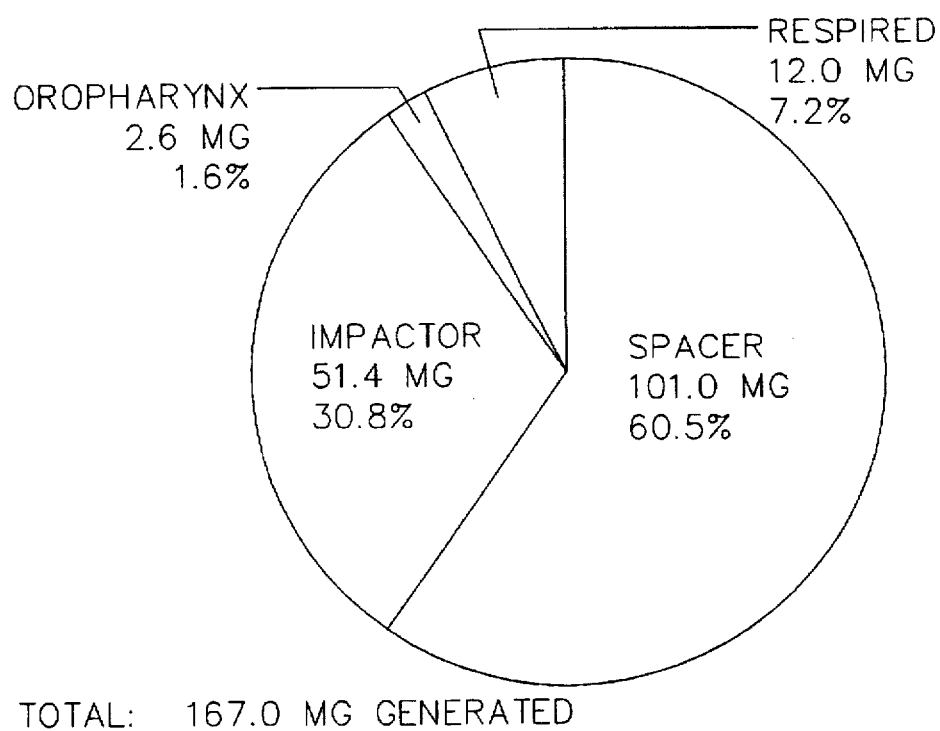
FIG. 11 is a chart of the fate of dry particle amiloride generated by the MDI with spacer and impactor when 12 mg of respirable amiloride are produced.

The fate of amiloride dispersed when generating a respirable dose of 12 mg is shown in FIGS. 9, 10, and 11 using the Spinhaler™ with impactor, the MDI with spacer alone, and the MDI with spacer and impactor. The distribution of amiloride shown in these pie diagrams comes directly from our results; the absolute mass of amiloride shown in each Figure is calculated from a ratio to the actual mass we obtained to show what is necessary to achieve the targeted therapeutic dose of 12 mg amiloride less than 4.7 um in diameter.

FIG. 9 shows that if the Spinhaler™ is used with the impactor, 137.5 mg per day of amiloride must be generated. Of this, 31.6 mg or nearly one quarter does not leave the Spinhaler™ at all but stays behind either as undispersed drug within the capsule (14.2%) or collects within the Spinhaler™ body (8.8%). The impactor collects 87.4 mg (63.6%) or most of the large particles so that the oropharyngeal dose is low at 6.4 mg (4.7%). As a result of the low oropharyngeal dose, the total systemic dose is low at 18.4 mg.

If the MDI is used with the spacer alone and no impactor is used, FIG. 10 shows that only 75.8 mg of amiloride needs to be generated. Of this, 50.8 mg (67%) collects in the spacer. The oropharyngeal dose is substantial at 13 mg (17.1%) so that the total systemic dose is somewhat high, 25 mg/day. However, if 8 mg respirable amiloride per day is the targeted therapeutic dose, then the oropharyngeal dose is reduced to 8.7 mg and the total systemic dose becomes an acceptable 16.7 mg/day.

FIG. 11 shows that if the MDI is used with the spacer and impactor, 167 mg must be generated daily to produce 12 mg of respirable amiloride. Almost all large particles are collected by the spacer (60.5%) or the impactor (30.8%) so that oropharyngeal deposition is very low, 2.6 mg/day (1.6%), and therefore the total systemic dose is acceptable at 14.6 mg/day.

Figure 12:
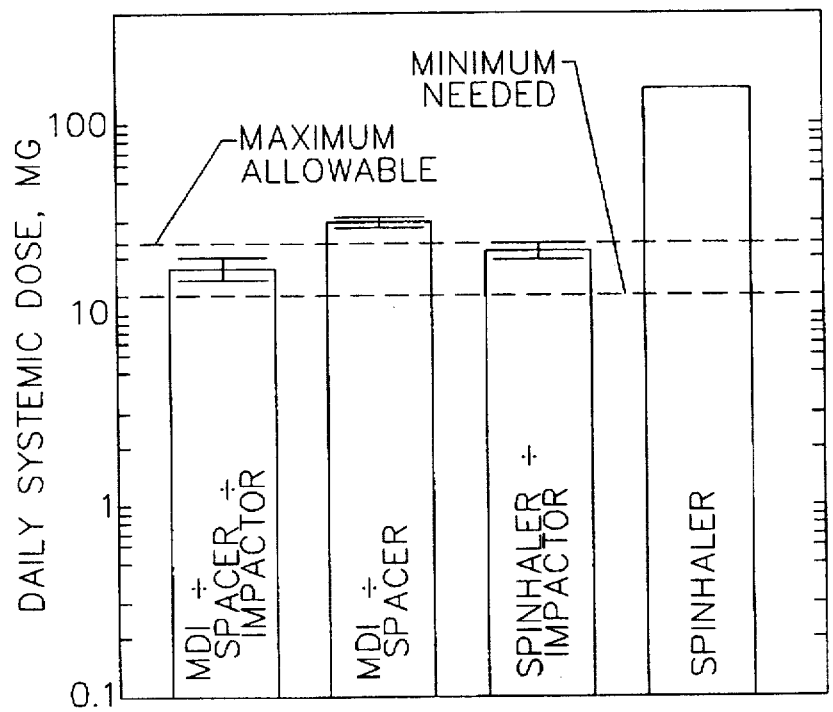
FIG. 12 is a graph of the daily systemic dose of amiloride delivered by the MDI with spacer and impactor, the MDI with spacer, the Spinhaler™ with impactor, and the spinhaler alone.

FIG. 12 shows the systemic dose delivered daily by each generation method. This figure shows that the oropharyngeal dose from the Spinhaler™ alone is far too high and results in an excessive systemic dose. However, the MDI with the spacer and impactor and the Spinhaler™ with impactor can deliver the required 12 mg/day of respirable amiloride without exceeding the maximum systemic dose of 20 mg/day. The MDI with spacer alone delivers a systemic dose somewhat higher than the maximum. If the daily therapeutic dose of amiloride is reduced to 8 mg/day, the MDI and spacer can generate this amount while limiting the total systemic daily dose to 16.7 mg.

Figure 13:
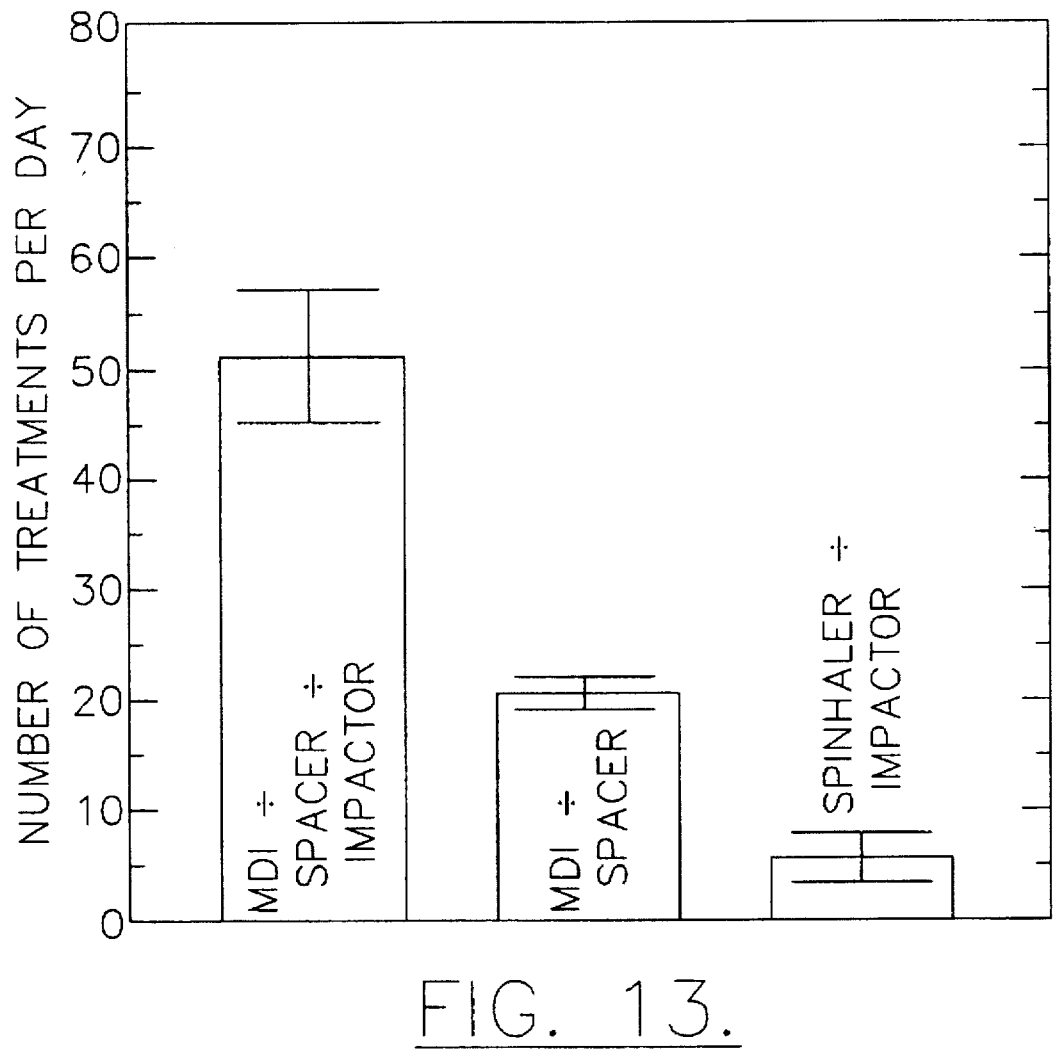
FIG. 13 is a graph of the number of drug treatments (MDI puffs or Spinhaler™ capsules) necessary to generate 12 mg/day of respirable amiloride for the MDI with spacer and impactor, the MDI with spacer, and the Spinhaler™ with impactor.

FIG. 13 shows the number of drug treatments per day required to generate 12 mg of respirable amiloride. If the Spinhaler™ is used with the impactor, the required 12 mg of respirable amiloride can be delivered in about five capsules. FIG. 13 shows that about 50 "puffs" per day are necessary if the MDI is used with the spacer and impactor; only about 20 "puffs" are required with the MDI and spacer alone. More or fewer capsules would be required if the capsules tested had more or less amiloride in them; similarly, the amount of amiloride per puff would change with differences in MDI design.

The foregoing Examples are illustrative of the present invention, and are not to be construed as limiting thereof. The invention is defined by the following claims, with equivalents of the claims to be included therein.

That which is claimed is:

1. A method of removing retained mucus secretions from the lungs of a human subject in need of such treatment, consisting essentially of:

generating an aerosol suspension of respirable solid, dry particulate amiloride, wherein said solid particulate amiloride is comprised of particles of about 1 to 5 microns, wherein said aerosol suspension is free of liquid amiloride particles; and then delivering by inhalation said aerosol suspension of respirable solid particulate amiloride to the respiratory system of said subject in an amount sufficient to achieve concentrations of amiloride on the airway surfaces of said subject of from about $10^{-7}$ to $10^{-3}$ Moles/liter, wherein the daily dose of said solid particulate amiloride is from about 1 to about 20 milligrams, and wherein said solid particulate amiloride is comprised of particles of about 1 to 5 microns, and whereby said secretions are hydrated and transported from the lung via mucociliary action.

2. A method according to claim 1, wherein said solid particulate amiloride is administered to the respiratory system of said subject in an amount sufficient to achieve concentrations of amiloride on the airway surfaces of said subject of from $10^{-6}$ to about $10^{-4}$ moles/liter.

3. A method according to claim 1, wherein said aerosol consists essentially of particles of amiloride having a particle size within the range of about 1 to 5 microns.

4. A method according to claim 1, wherein said solid particulate amiloride comprises a pharmaceutically acceptable salt of amiloride.

5. A method according to claim 1, wherein said solid particulate amiloride comprises a free base of amiloride.

6. A method according to claim 1, wherein said solid particulate amiloride comprises a mixture of a free base of amiloride and a pharmaceutically acceptable salt of amiloride.

7. A method according to claim 1, wherein said solid particulate amiloride further comprises a dispersant.

8. A method according to claim 7, wherein said dispersant comprises lactose.

9. A method of treating cystic fibrosis in a human subject in need of such treatment, consisting essentially of:

generating an aerosol suspension of respirable solid, dry particulate amiloride, wherein said solid particulate amiloride is comprised of particles of about 1 to 5 microns, and wherein said aerosol suspension is free of liquid amiloride particles; and then delivering by inhalation said aerosol suspension of respirable solid particulate amiloride to the respiratory system of said subject in an amount sufficient to achieve concentrations of amiloride on the airway surfaces of said subject of from about $10^{-7}$ to $10^{-3}$ Moles/liter, wherein the daily dose of said solid particulate amiloride is from about 1 to about 20 milligrams, and wherein said solid particulate amiloride is comprised of particles of between about 1 to 5 microns, whereby mucus secretions in the lungs of said subject are hydrated and transported from the lung via mucociliary action.

10. A method according to claim 9, wherein said aerosol consists essentially of particles of amiloride having a particle size within the range of about 1 to 5 microns.

11. A method according to claim 9, wherein said solid particulate amiloride is administered to the respiratory system of said subject in an amount sufficient to achieve concentrations of amiloride on the airway surfaces of said subject of from $10^{-6}$ to about $10^{-4}$ moles/liter.

12. A method according to claim 9, wherein said solid particulate amiloride comprises a mixture of a free base of amiloride and a pharmaceutically acceptable salt of amiloride.

13. A method according to claim 9, wherein said solid particulate amiloride comprises a free base of amiloride.

14. A method according to claim 9, wherein said solid particulate amiloride comprises a mixture of a free base of amiloride and a pharmaceutically acceptable salt of amiloride.

15. A method according to claim 9, wherein said solid particulate amiloride further comprises a dispersant.

16. A method according to claim 15, wherein said dispersant comprises lactose.

* * * * *